(12) United States Patent
Makarov et al.

(10) Patent No.: US 8,642,948 B2
(45) Date of Patent: Feb. 4, 2014

(54) ION TRAP FOR COOLING IONS

(75) Inventors: Alexander A. Makarov, Bremen (DE); Eduard V. Denisov, Bremen (DE)

(73) Assignee: Thermo Fisher Scientific (Bremen) GmbH, Bremen, DE (US)

( * ) Notice: Subject to any disclaimer, the term of this patent is extended or adjusted under 35 U.S.C. 154(b) by 0 days.

(21) Appl. No.: 13/062,784

(22) PCT Filed: Sep. 11, 2009

(86) PCT No.: PCT/EP2009/061822
§ 371 (c)(1),
(2), (4) Date: Mar. 8, 2011

(87) PCT Pub. No.: WO2010/034630
PCT Pub. Date: Apr. 1, 2010

(65) Prior Publication Data
US 2011/0163227 A1    Jul. 7, 2011

(30) Foreign Application Priority Data
Sep. 23, 2008   (GB) .................................. 0817433.6

(51) Int. Cl.
*B01D 59/44* (2006.01)

(52) U.S. Cl.
USPC ............................ 250/283; 250/281; 250/282

(58) Field of Classification Search
None
See application file for complete search history.

(56) References Cited

U.S. PATENT DOCUMENTS

| | | | |
|---|---|---|---|
| 2,448,568 A * | 9/1948 | Zwillinger et al. ............... | 353/5 |
| 2,463,149 A * | 3/1949 | Caine ....................... | 128/200.26 |
| 5,373,156 A * | 12/1994 | Franzen ........................ | 250/288 |
| 5,969,349 A * | 10/1999 | Budovich et al. .............. | 250/286 |
| 6,730,904 B1 * | 5/2004 | Wells ............................ | 250/292 |
| 6,911,650 B1 * | 6/2005 | Park .............................. | 250/292 |
| 6,972,408 B1 | 12/2005 | Reilly | |
| 7,189,967 B1 * | 3/2007 | Whitehouse et al. ......... | 250/292 |
| 7,211,792 B2 | 5/2007 | Yamaguchi | |
| 7,256,395 B2 * | 8/2007 | Collings et al. ............... | 250/288 |
| 7,259,371 B2 * | 8/2007 | Collings et al. ............... | 250/288 |
| 2001/0054685 A1 * | 12/2001 | Franzen ........................ | 250/287 |
| 2002/0175278 A1 * | 11/2002 | Whitehouse ................... | 250/281 |
| 2004/0065824 A1 * | 4/2004 | Bateman et al. .............. | 250/288 |
| 2004/0089799 A1 * | 5/2004 | Kawato et al. ................. | 250/281 |
| 2004/0164240 A1 * | 8/2004 | Okumura et al. ............. | 250/288 |
| 2005/0056776 A1 * | 3/2005 | Willoughby et al. ......... | 250/281 |
| 2006/0151692 A1 * | 7/2006 | Collings et al. ............... | 250/290 |
| 2006/0169891 A1 * | 8/2006 | Collings et al. ............... | 250/291 |

(Continued)

FOREIGN PATENT DOCUMENTS

| | | |
|---|---|---|
| DE | 196 27 621 A1 | 1/1998 |
| DE | 102 21 468 A1 | 7/2003 |

(Continued)

*Primary Examiner* — Andrew Smyth
(74) *Attorney, Agent, or Firm* — Charles B. Katz

(57) ABSTRACT

A method of changing the kinetic energy of ions is provided, comprising: trapping ions in a trapping region of an ion trap; and directing a beam of gas through the trapping region, so as to change the kinetic energy of the trapped ions thereby. Also provided is a method of separating ions, the method comprising: causing ions to enter a trapping region of an ion trap along a first axis of the trapping region; directing a beam of gas along the first axis and applying an electric potential in the direction of the first axis so as to cause separation of the ions based on their ion mobility. An ion trap and a mass spectrometer for performing the methods are also provided.

29 Claims, 2 Drawing Sheets

(56) References Cited

U.S. PATENT DOCUMENTS

| | | | |
|---|---|---|---|
| 2008/0006768 A1* | 1/2008 | Yamaguchi | 250/287 |
| 2008/0164409 A1* | 7/2008 | Schultz et al. | 250/282 |
| 2008/0277580 A1* | 11/2008 | Takeshita et al. | 250/292 |
| 2009/0309015 A1* | 12/2009 | Schultz et al. | 250/281 |
| 2010/0065740 A1* | 3/2010 | Iwamoto et al. | 250/288 |
| 2010/0116982 A1* | 5/2010 | Iwamoto et al. | 250/292 |
| 2011/0095180 A1* | 4/2011 | Taniguchi | 250/287 |
| 2011/0163227 A1* | 7/2011 | Makarov et al. | 250/282 |

FOREIGN PATENT DOCUMENTS

| | | | | |
|---|---|---|---|---|
| DE | 10221468 A1 * | 7/2003 | | H01J 49/42 |
| GB | 2 448 568 A | 10/2008 | | |
| GB | 2 463 149 A | 3/2010 | | |
| WO | WO 2004/109741 A2 | 12/2004 | | |
| WO | WO 2004109741 A2 * | 12/2004 | | H01J 49/00 |
| WO | WO 2006/103412 A2 | 10/2006 | | |
| WO | WO 2006103412 A2 * | 10/2006 | | H01J 49/04 |
| WO | WO 2007071991 A2 * | 6/2007 | | H01J 49/04 |

\* cited by examiner

ION TRAP FOR COOLING IONS

TECHNICAL FIELD

This invention relates to an ion trap for changing the kinetic energy of ions and a method of changing the kinetic energy of ions in an ion trap, preferably to cool the ions.

BACKGROUND TO THE INVENTION

For high resolution mass spectrometers, it is desirable that ions for analysis have a low emittance, since this improves resolving power and sensitivity. The ion beam emittance is in part determined by its temperature. Traditionally, ions are cooled by collisions with a gas. However, since the mass analyser operates at a high vacuum, it is desirable to cool the ions outside of the mass analyser.

Existing solutions have followed two divergent strategies. A first strategy is to cool the ions in a trap, external to the mass analyser, which contains a gas suitable for cooling the ions, for example as shown in U.S. Pat. No. 6,674,071. However, in such devices, the ions can only be cooled to the temperature of the gas, which is limited to that of the ion optics of the trap, since the gas is effectively held within the trap, in thermal equilibrium with the material with which it is trapped. This places a limit on the minimum achievable emittance of the cooled ion beam.

Moreover, when the trap is used for injecting the cooled ions into the mass spectrometer, further problems arise. Accelerating the ions through the gas can cause fragmentation of the ions and removing the gas before ejecting the ions limits the speed of operation significantly. If the ions are accelerated using electric fields, as is typically done, although all ions are accelerated to a constant energy, their velocity will depend on their mass. Hence, the path length from trap to analyser must be minimised in such cases, to mitigate time-of-flight mass separation outside of the analyser. This turns prevention of gas carry-over into the analyser into a serious problem. This problem is typically alleviated by avoiding line-of-sight between the trap and the analyser and by using small apertures, at the expense of increased cost and complexity and reduced performance. Also, this further increases path length, thereby worsening any external mass separation problems.

In an implementation of this strategy, it is known to introduce the gas as pulses. This assists in reducing gas load during analysis after ion cooling. Older examples of this include: J. Carlin and B. S. Freiser, Anal. Chem. 55 (1983), 571; B. Emary, R. E. Kaiser, H. I. Kenttamaa and R. G. Cooks, J. Am. Soc. Mass Spectrom. 1 (1990) 308; and R. C. Beavis and B. T. Chait, Chem. Phys. Lett. 181 (1991) 479.

Other, more recent examples of this technique include: GB-2439107; and D. Papanastasiou, O. Belgacem, M. Sudakov and E. Raptakis, Rev. Sci. Instrum. 79 (2008) 055103. However, there is no fundamental difference between this technique and the static operation. In both techniques, gas enters the ion trap in a highly diffused manner.

The second strategy has been to direct the ion beam through a gas jet. For example, U.S. Pat. No. 5,373,156 describes a method for cooling very heavy ions (300,000 to 2 million Da) using a light gas, such as hydrogen or helium, which is adiabatically cooled during formation and directed as a jet. The gas jet also causes the ions to decelerate immediately upstream of the mass analyser, thereby avoiding potential fragmentation or mass separation problems. However, such devices are not compatible with trapping, since they are designed to allow the cooled ions to be injected into the mass analyser immediately. Furthermore, gas carry-over remains a problem with such devices.

Gas jets have been used for collision induced dissociation (CID) of ions. In U.S. Pat. No. 4,328,420, a mass spectrometer is disclosed having three quadrupole sections with the middle section acting as a collision cell with a gas jet intercepting the ion beam in an orthogonal manner. Similar arrangements for CID with a gas jet entering a collision cell and intercepting an ion path in an orthogonal manner are disclosed in US 2004/0119015 and US 2007/0085000, including arrangements with an ion trap. Such ion traps additionally employ a significant pressure of bath gas in the trap for storage of the ions thus significantly adding to the gas load of the system.

SUMMARY OF THE INVENTION

Against this background, the present invention provides a method of changing the kinetic energy of ions, comprising: trapping ions in a trapping region of an ion trap; and directing a beam of gas through the trapping region, so as to change the kinetic energy of the trapped ions thereby.

The present invention in another aspect provides a method of separating ions, the method comprising: causing ions to enter a trapping region of an ion trap along a first axis of the trapping region; directing a beam of gas along the first axis and applying an electric potential in the direction of the first axis so as to cause separation of the ions based on their ion mobility.

Preferably, the gas is a cooling gas, such that the trapped ions are cooled. The method preferably comprises storing the ions in the trapping region, i.e. for a time period until it is desired to eject the ions from the trap. More preferably, the trapped ions are substantially not dissociated by the beam of gas. That is, a small minority of the ions may be dissociated by the beam, e.g. unintentionally, but the majority of the ions are not dissociated by the beam. Most preferably, the trapped ions are cooled but substantially not dissociated by the beam of gas.

Ions stored within the trap can thereby be cooled to a low temperature, and ejected from the trap into a mass analyser or into another device before mass analysis. This provides a significant degree of flexibility, since such ions can thereby be optimised for different types of mass analyser, including for instance, pulsed mass analysers. In contrast to prior art methods of gas jet cooling, it can be used with an ion beam that has undergone processing within the vacuum environment of the instrument, and not just for ion beams as they are introduced into the instrument.

All of the particles of a gas beam can be considered to have a vector of motion with a dominant component, the dominant component being common across all of the particles, such that the gas particles have a low divergence. As a result, the distribution of gas within the trap volume is non-uniform. Advantageously, the invention permits the efficient trapping and storage of ions in an ion trap with a much reduced bath gas pressure than normal as it has been found that the use of the directed beam of gas provides good ion storage and cooling capabilities due to sufficient collisions between the gas and the ions in the region of the beam. In this way, the ion trap of the invention may be operated at a lower pressure (i.e. away from the gas beam) than normally employed for ion traps which require the use of a large pressure of bath gas. Thus, the invention enables the gas load on the rest of the mass spectrometer system to be correspondingly reduced. Accordingly, the invention is preferably operated with a pressure in the ion trap (i.e. away from the beam) which on its own would be too low to store ions in the trap, especially to trap, store and cool ions. For example, whereas a typical pressure in an ion trap using bath gas may be about $1\times10^{-3}$ mbar, the pressure in the ion trap according to the invention may be less than $1\times10^{-4}$ mbar. Preferably, the pressure in the ion trap is about $1\times10^{-4}$ mbar or less, more preferably less than $1\times10^{-4}$ mbar, still more preferably about $5\times10^{-5}$ mbar or less, e.g. in the region of $1\times10^{-5}$ mbar. In a preferred embodiment, the method further comprises receiving ions at the trap.

Preferably, the trapping region comprises a first axis. The first axis is preferably a long axis of the trapping region, i.e. an axis in the direction of the length or longest dimension of the trapping region. The trapped ions preferably traverse the trapping region repeatedly along the first axis. The first axis may be straight or curved or a combination of straight and curved sections. Accordingly, preferably, the ion trap is elongated (i.e. is longer in the elongate direction than the directions orthogonal thereto) along the first axis. That is, the trap is preferably an elongate trap having a long axis arranged substantially collinearly with the direction of the beam. In such embodiments, preferably ejection of the ions from the trap is in a different direction, i.e. at an angle (preferably orthogonally), to the gas beam direction. More preferably, the beam of gas is directed substantially along the first axis. This means that divergence of the beam is preferably such that at least part of the beam envelops at least part of the first axis. Thus, the dominant component of the vector of motion of the gas particles is directed along the first axis. Most preferably, the ion trap is a linear ion trap, elongated along the first axis. Thus, the trapped ions interact with the beam of gas over a substantial interaction length. Further preferably, the ions to be trapped in the trapping region are injected into the trap substantially along the first axis. In one preferred embodiment type, the beam of gas is directed substantially along the first axis but in an opposite direction to ions that are injected into the trap substantially along the first axis. In another preferred embodiment type, the beam of gas is directed substantially along the first axis in the same direction that the ions are injected into the trap substantially along the first axis. Trapped ions preferably are ejected from the ion trap along a second axis, where the second axis is different from the first axis. Thus, in preferred embodiments, the ions may be ejected from the ion trap along a different axis from the axis along which they entered the trap. In this way, the risk of fragmentation of the ion due to their acceleration through the gas is advantageously mitigated. Since the gas is directed along the first axis, by ejecting the ions along the second axis, the ions are not accelerated along the gas beam, but are accelerated out of the gas beam. More preferably, the second axis is substantially orthogonal to the first axis, minimising the path length the ions travel within the gas beam as they are accelerated. Preferably, the proportion of the beam of gas travelling in the direction of the second axis is significantly smaller than the proportion of the beam of gas travelling in the direction of the first axis. Advantageously, the flow rate of the gas along the second axis is substantially zero. The trap is thus preferably a low pressure trap. The trap is more preferably not uniformly pressurised with a gas for changing the kinetic energy of the ions, i.e. a bath gas.

In a preferred embodiment, the step of directing a beam of gas comprises forming a gas jet. A gas jet is a stream of gas with a single preferred direction of motion that is projected into a surrounding medium. Preferably, the method also comprises receiving the gas at a gas inlet or nozzle. In this case, the pressure within the ion trap may be significantly less than the pressure outside of the gas inlet. This causes the gas to be adiabatically cooled when entering the ion trap through supersonic expansion. Optionally, the temperature of the gas inside the ion trap is significantly less than the temperature of the received ions. Optionally, the temperature of the gas inside the ion trap is significantly less than the temperature of the ion trap. The gas beam may be directed through the trapping region continuously while the ions are trapped or stored in the trapping region or the gas beam may be directed through the trapping region intermittently, e.g. by pulsing the gas beam. The gas beam may be directed through the trapping region for the whole time or for less than the whole time that the ions are trapped or stored in the trapping region.

In a preferred embodiment, a portion of the beam of gas entering the trapping region exits the ion trap before colliding with a wall. Optionally, this portion of the beam of gas is at least 10%, but in increasing order of preference it may be at least 20%, at least 30%, at least 50%, at least 75%, or at least 90%.

Optionally, the ion trap comprises a differential pumping aperture arranged along the first axis. The method may then further comprise: creating a region of first pressure on the side of the differential pumping aperture that is closer to the gas inlet; and creating a region of second pressure on the other side of the differential pumping aperture, the second pressure being lower than the first pressure.

Preferably, the differential pumping aperture is formed using a skimmer cone. Advantageously, the skimmer cone is located between the gas inlet and the location identified for the Mach disk of the gas flowing through the gas inlet. Equivalently, the skimmer cone is located such that the gas flowing through the gas inlet is sampled under free-jet conditions. Advantageously, the entrance aperture is arranged to receive a potential so as to cause ion mobility separation of the ions. Beneficially, the ion trap is arranged such that this ion mobility separation occurs along the first axis of the ion trap. More generally, in various embodiments, the method of the invention preferably comprises applying a potential gradient through the trapping region so as to cause separation of the ions based on their mobility. More preferably in such embodiments, the method comprises directing the beam of gas along the first axis and applying an electric potential gradient in the direction of the first axis so as to cause separation of the ions based on their ion mobility along the first axis. Beneficially, the ion trap is arranged such that the ion mobility separation of the ions occurs along the first axis of the ion trap, i.e. spatial separation occurs along this axis. Preferably, the separated ions are ejected from the trap along a second axis which is different to, and more preferably not collinear with, the first axis, e.g. the second axis is orthogonal to the first axis. Preferably, an electric potential gradient is applied in the direction of the first axis to produce a counteracting electric force to the force from the beam of gas so that ions of a particular ion mobility will equilibrate at a particular point on this potential gradient, i.e. where these two forces compensate each other, i.e. so that ion mobility separation in space can be performed. If the potential gradient is varied or scanned, ion mobility-dependent extraction (scanning) of ions may be implemented. An ion trap having an axial electric field is taught by U.S. Pat. No. 5,847,386 but the use of a beam of gas directed through the trap is not disclosed therein.

The ions can be trapped in a number of different configurations. In a preferred embodiment, the step of trapping received ions uses a set of quadrupole rods. Alternatively, the step of trapping received ions in the ion trap comprises directing the ions to travel along a circuit path, the circuit path including the first axis. For example, a race-track arrangement of electrodes might be used to provide the circuit.

In a second aspect of the invention, an ion trap for changing the kinetic energy of ions is provided. The ion trap comprises: an electrode arrangement; a pumping arrangement; and a controller, arranged to control the electrode arrangement to trap received ions in a trapping region, and to control the pumping arrangement to cause a beam of gas to be directed through the trapping region, so as to change the kinetic energy of the trapped ions thereby. Preferably, the gas is a cooling gas, so as to be arranged for cooling of the ions.

The trapping region preferably comprises a first axis. The controller is preferably further configured to control the electrode arrangement to eject trapped ions from the ion trap along a second axis, the second axis being different from the first axis. Optionally, the second axis is orthogonal to the first axis.

In a preferred embodiment, the controller is further arranged to control the pumping arrangement so as to form a gas jet. Optionally, the controller is further arranged to control the pumping arrangement such that the pressure within the ion trap is significantly less than the pressure on the other side of the gas inlet from the ion trap.

In some embodiments, the ion trap may also comprise: a differential pumping aperture arranged along the first axis. In this case, the controller may be further arranged to control the pumping arrangement to create a region of first pressure on the side of the differential pumping aperture that is closer to the gas inlet, and to create a region of second pressure on the other side of the differential pumping aperture. The second pressure is advantageously lower than the first pressure.

The differential pumping aperture is optionally formed using a skimmer cone. Preferably, the skimmer cone is located between the gas inlet and the location identified for the Mach disk of the gas flowing through the gas inlet. Equivalently, the skimmer cone is located such that the gas flowing through the gas inlet is sampled under free-jet conditions. Advantageously, the method further comprises: causing the ions to enter the ion trap, before being trapped, through an entrance aperture; and applying a potential to the entrance aperture so as to cause ion mobility separation of the ions. This ion mobility separation is beneficially performed along the first axis of the ion trap.

In one embodiment, the electrode arrangement comprises a set of quadrupole rods. In an alternative embodiment, the electrode arrangement is configured in a circuit path including the first axis, and wherein the controller is further arranged to control the electrode arrangement such that the ions are directed to travel along the circuit path.

In a further aspect of the present invention, there is provided an ion trap for changing the kinetic energy of ions, comprising: means for trapping received ions in a trapping region of the ion trap; and means for directing a beam of gas through the trapping region, so as to cool the trapped ions thereby. Preferably, the gas is a cooling gas, so as to be arranged for cooling of the ions.

In an additional aspect of the present invention, a mass spectrometer is provided, comprising an ion trap as previously described and a mass analyser, arranged to receive cooled ions from the ion trap. The mass spectrometer preferably also comprises an ion source, arranged to generate ions. Optionally, the ion trap may be a first ion trap and a second trap may be provided, located between the ion source and the first ion trap. In this case, the second ion trap is advantageously gas-filled. In the preferred embodiment, the mass analyser comprises one of: an orbitrap-type mass analyser; a time-of-flight mass analyser; or a time-of-flight mass analyser comprising at least one of multi-turn or multi-reflecting configurations.

In still another aspect of the present invention, there is provided an ion mobility separation apparatus, comprising: an ion trap having a trapping region comprising a first axis; means for directing a beam of gas through the trapping region along the first axis; and means for applying an electric field in the direction of the first axis. The apparatus preferably further comprises means for causing ions to enter the trapping region along the first axis, more preferably in the opposite direction to the beam of gas.

In preferred embodiments, the ion trap is located intermediate between an ion source for generating the ions to be trapped and means for directing the beam of gas through the trapping region, wherein the ion trap, ion source and means for directing the beam of gas through the trapping region are arranged in a substantially linear (i.e. straight line) configuration. The ion source and means for directing the beam of gas through the trapping region in such embodiments further preferably lie substantially on the first axis of the trapping region.

In some embodiments, the method may further comprise modulating the gas beam or jet. Preferably, the density of the gas beam is modulated in time. Advantageously, ions are ejected when the density of the gas beam in the trapping region is below a predetermined maximum level.

Such modulation is preferably performed by a pulsed valve, to produce a series of gas plugs travelling through the trapping region. For example, this may allow cooling of ions when the gas plugs are transmitted, and extraction of the ions during the gap time between plugs. This may further reduce any interaction between ions and gas during the extraction process. In an embodiment, a further valve is located in the path along which the extracted ions travel. This valve is opened only to allow ions to travel towards the analyser. This reduces the gas load on the analyser from the trapping region and other regions outside the analyser, and may avoid the use of differential pumping, saving complexity and cost. The pulsed valve may comprise a piezoelectric or electromagnetic arrangement for example, and may operate in a pulsed manner or in a harmonically oscillating manner, synchronised to the injection of ions from the trapping region into the analyser.

BRIEF DESCRIPTION OF THE DRAWINGS

The invention may be put into practice in various ways, a number of which will now be described by way of example only and with reference to the accompanying drawings in which.

SPECIFIC DESCRIPTION OF A PREFERRED EMBODIMENT

Figure 1:
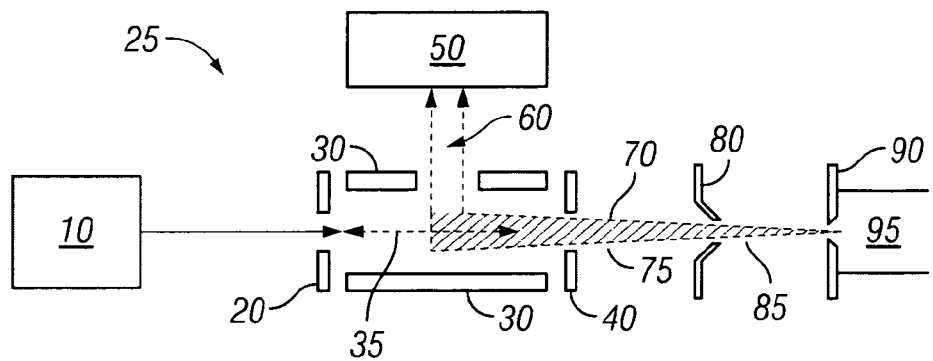
FIG. 1 shows a first and preferred embodiment of a method and mass spectrometer according to the invention.

Referring first to FIG. 1, there is shown a first embodiment of a mass spectrometer according to the invention. Ions are introduced from an ion source 10 through a first aperture 20 into an ion trap 25 defined by an extended set of rods 30, which are preferably quadrupolar. The rods 30 define a longitudinal axis 35, bounded by the first aperture 20 and a second aperture 40. Mass analyser 50 is provided adjacent the ion trap in a direction perpendicular to the longitudinal axis.

An external gas line 95 is coupled to nozzle 90 and skimmer cone 80, adjacent to the nozzle, defines a differential pumping aperture.

An RF potential is applied to the rods 30 of the ion trap 25, such that the ions are directed along the longitudinal axis 35 of the ion trap. The ions are confined axially by voltages applied to first aperture 20 and second aperture 40. Gas enters the mass spectrometer from external gas line 95 through the nozzle 90 into a first pumping region 85. It thereby forms a gas jet 70 by supersonic expansion of the gas received from the external gas line 95 into pumping region 85. Skimmer cone 80 is located sufficiently remote from the nozzle 90 to ensure low divergence of the gas jet 70. The gas jet 70 is then directed through a second pumping region 75 and along longitudinal axis 35.

By interaction with the ions, the gas jet thereby cools the ions trapped within the ion trap 25. Once cooled, the ions can be ejected orthogonally along ejection axis 60, into mass analyser 50 for analysis. Mass analyser 50 is an Orbitrap™.

Gas pressures, temperatures, pumping as well as geometrical parameters of the nozzle 90 and skimmer cone 80 are chosen in such a way that the skimmer tip penetrates through the Mach disk into the free jet (for example, see Beijerinck et al, Chem. Phys. 96 (1985) 153-173 and references therein). For example, Nitrogen or Argon at atmospheric conditions could be used to expand through a nozzle of 50 microns diameter into the region 85 pumped by a 200 L/s turbomolecular pump. The gas jet Mach disk is located at about 24 mm from the nozzle 90, the skimmer 80 then could be located at about 12-15 mm from the nozzle 90.

The size and shape of skimmer cone 80 are preferably chosen in a way that minimises formation of detached shock waves that could reduce the flow through the skimmer cone 80. For example, an internal diameter of 1 mm, sharp edges and full angles of 70 degrees (inner) and 90 degrees (outer) of skimmer cone 80 are preferred. The ion trap is located close to the skimmer, for example 10-20 mm away from it. The required gas flow in the trap could be roughly estimated using known gas thickness for conventional collisional cooling (approximately $(1 \ldots 3)*10^{19}$ mol/m$^2$). At these conditions, cooling occurs over several milliseconds. Accelerated cooling could be achieved by increasing the gas density, which in turn is achieved by increased pressure in a gas reservoir supplying external gas line 95.

Unlike conventional ion traps, there is no need to enclose the trap to produce a locally high pressure: on the contrary, a more "opened" construction of rods allows to minimise collisions during ion extraction from trap 25 into mass analyser 50.

Alternatives and improvements to the embodiment described above are possible. The low temperature of the gas jet molecules can be used to achieve deep cooling of received ions. This is achieved if the ions move at approximately the same speed as the jet, being confined at the same time by RF fields.

Figure 2:
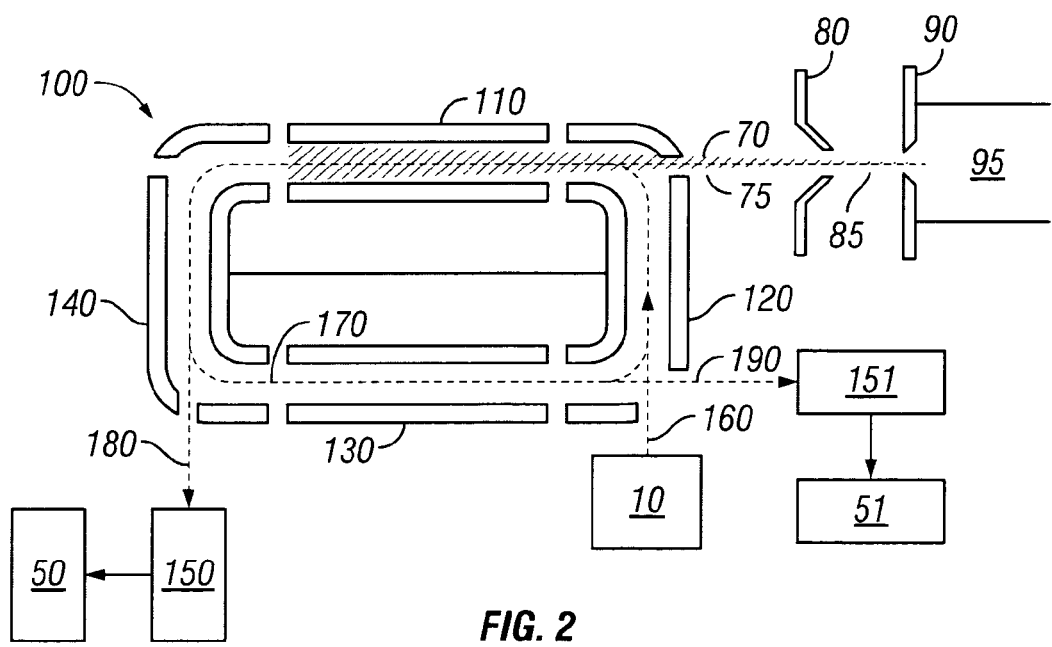
FIG. 2 shows a second embodiment of a method and mass spectrometer according to the invention.

An implementation of this principle is illustrated in FIG. 2, in which there is shown a second embodiment of a mass spectrometer according to the present invention. Where the same features are shown as in FIG. 1, identical reference numerals are used. An ion trap 100 is formed in a race-track shape, comprising a first segment 110, second segment 120, third segment 130 and fourth segment 140.

Ions generated in ion source 10 are directed towards the ion trap 100. The potential applied to segment 120 of the ion trap 100 is switched off, for example, for several tens microseconds, to allow ions to arrive. Injected ions move along the circumference of ion trap 100. Gas jet 70 is generated through nozzle 90 and skimmer cone 80 and thereby directed towards segment 110. The ions trapped in the ion trap 100 periodically pass through the gas jet 70 and become more and more equilibrated with gas molecules, both in speed and temperature. It will be appreciated that directing of the beam through the trapping region as referred to herein means directing the beam through at least part of the trapping region. For example, in FIG. 2, the gas jet is directed through the part of the trapping region which is segment 110.

After a number of circuits, ions reach equilibrium and are ready for extraction. Then, segment 140 of the ion trap 100 is switched off to allow ions to pass into pulser 150. From here ions are injected into mass analyser 50. As ions of different m/z have essentially similar velocities, mass discrimination during transfer from ion trap 100 to pulser 150 is minimised.

To increase the duty cycle, an alternative arrangement could be employed, which is also shown in FIG. 2. Ions could be stopped in their race-track movement within segment 130 by applying a reflecting potential on segments 140 and 120 once ions have arrived within segment 130, and then gradually decreasing the voltage on the previous segment 130 to provide adiabatical trapping of ions within segment 130. As the pressure in segment 130 is very low, internal ion temperatures stay unperturbed.

At the end of this squeezing process, ions are released into alternative pulser 151 by removing the reflecting potential from segment 120. The ions are then ejected to alternative mass analyser 51. However, there is an increased energy spread resulting from the squeezing in this arrangement.

Figure 3:
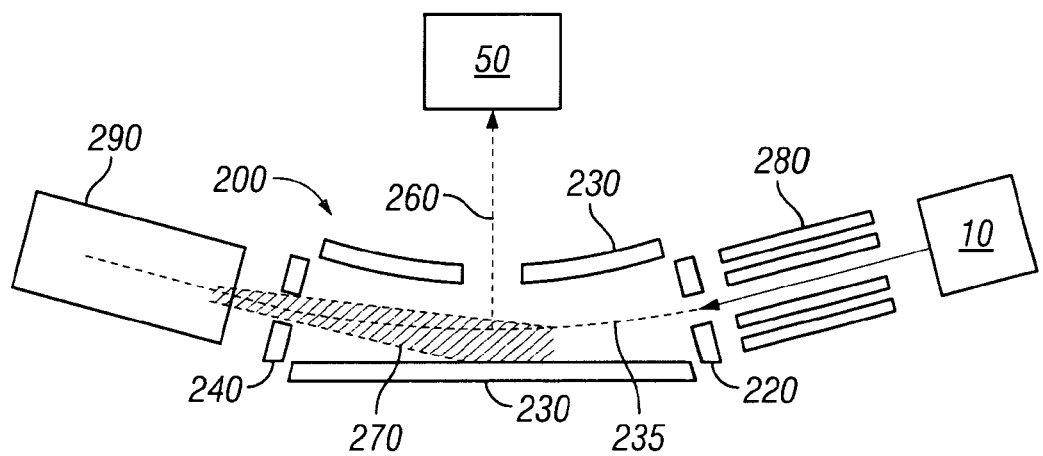
FIG. 3 shows a third embodiment of a method and mass spectrometer according to the invention.

Referring to FIG. 3, there is shown a third embodiment according to the present invention. Where the same features are shown as in FIGS. 1 and 2, identical reference numerals are used. An ion trap 200 is provided which is of a C-trap form, as described e.g. in WO 2008/081334, defined by elongate electrodes 230 at least some of which are curved along their long axis. The elongate electrodes 230 define a long axis 235 of the trapping region which is thus slightly curved. A mass analyser 50 is provided adjacent the C-trap 200 in a direction orthogonal to the long axis 235 of the trapping region. The C-trap 200, like the ion trap 25 of FIG. 1, is open to its surroundings, which is not typical for ion traps which are normally operated at elevated pressure compared to their surroundings, the elevated pressure being maintained by an enclosure and a supply of collision gas. Instead the C-trap 200 is operated with a low internal pressure in the trap of typically about $1\times10^{-4}$ mbar or less, which is less than pressures normally found in ion traps. The pressure of the immediate surroundings of the trap is typically about $1\times10^{-5}$ to $1\times10^{-6}$ mbar.

Ions are introduced into the ion trap 200 substantially along the long axis 235 from an ion source 10, via an octapole guide 280 and a first aperture 220. An RF potential is applied to the electrodes 230 of the ion trap 200, such that the ions are directed along the long axis 235 of the ion trap. The ions are confined axially by voltages applied to the first aperture 220 and a second aperture 240.

A collision cell 290 in communication with the C-trap 200 is operated at elevated pressure compared to the trap 200. The pressure in the collision cell 290 within its enclosure is in the range $1\times10^{-2}$ mbar to $1\times10^{-3}$ mbar. The pressure differential between the collision cell 290 and the C-trap 200 in this example is about 100-fold. Gas from the collision cell 290 enters the C-trap 200 through an opening in the collision cell (not shown) and through aperture 240. The shape and configuration of the collision cell 290 (e.g. the shape of the enclosure of the collision cell and the arrangement of rods or stacked plates within the collision cell) aid the formation of a beam 270 of the gas which proceeds substantially along long axis 235 with low divergence, albeit with more divergence than a supersonic gas jet. The slightly curved nature of the long axis 235 of the trapping region is thus counteracted by the slight divergence of the gas beam 270. By interaction with the ions, the gas beam 270 cools the ions trapped within the C-trap 200. Once cooled, the ions can be ejected orthogonally along ejection axis 260, into mass analyser 50 for analysis. Mass analyser 50 is an Orbitrap™.

It can be seen that the directions of ion injection, long axis of the trapping region and the gas beam are substantially collinear (i.e. within a small angle of tolerance) and that ejection from the C-trap is at an angle to the long axis.

The gas load from the beam 270 is dissipated through the ion entrance aperture 220 and the through the top and bottom of the C-trap 200.

In an alternative or additional mode of operation, ions enter the C-trap 200 (optionally with intermediate storage in the C-trap), are ejected from the C-trap along long axis 235 to the collision cell 290, are fragmented and/or reacted in the collision cell 290, and are then injected back into the C-trap 200 from the collision cell 290 together with the gas beam 270.

Whilst specific embodiments have been described, the skilled person may contemplate various modifications and substitutions. A controller may be provided to control the ion trap, for example the potentials on the rods of the trap, and the pumping arrangement. For example, although a quadrupole ion trap 25 with straight rods 30 is considered, the rods may alternatively be curved and the longitudinal axis would likewise be curved. Also, although quadrupolar rods are used above, these could alternatively be hexapolar, octopolar or any other extended rod or plate configurations, as the skilled person would recognise. Similarly, although mass analyser 50 is an Orbitrap™, the skilled person will understand that mass analysers of similar type such as trapping mass analysers, or of time-of-flight type. A time-of-flight type mass analyser may include multi-reflection and additionally or alternatively multi-turn analysers. The proposed solution is of particular benefit for these types of analysers because they are especially sensitive to the residual gas pressure. This is particularly so for higher mass ions. Moreover, the resolving power of these analysers increases when the initial energy spread of ions is reduced.

If jet expansion is effected without generating shock waves, the gas molecules may be cooled to between 10 K and 30 K, with a low spread of velocities. During trapping of the ions, this cooling will affect the ions and cause significant reduction of their kinetic and internal energies (especially at low ion numbers and hence negligible space charge effects). This in turn will improve analytical parameters of the aforementioned analyser such as resolving power, mass accuracy, transmission, etc. For macromolecular ions (such as proteins or DNA), reduction of internal energy provides an added advantage of reduced metastable decay during the flight in mass analyzer.

The skilled person will appreciate that there are many different ways to obtain a gas jet 70. Although an external gas line 95 is described herein, this could instead simply be atmosphere. Skimmer cone 80 could alternatively act as the aperture 40. A turbo-molecular pump has been described above in generating a gas jet, but the skilled person would recognise that a rotary pump may alternatively be used.

In a preferred implementation of the first embodiment, ion trap 25 could be combined with a more traditional gas-filled ion trap, located between the ion source 10 and the ion trap 25. This could be used for pre-cooling of ions (i.e. removal of the major part of initial kinetic energy). For this, it would be sufficient to use this additional trap as a sink for the gas jet after it passes through ion trap 25 and then restrict conductivity of pumping to <1 L/s. Of course, gas could be also delivered from a dedicated gas line or previous pumping region 85.

Although a static gas jet has been described above, other forms of gas jet are possible. In a further embodiment, a gas jet is modulated by a pulsed valve, which is located near to nozzle 90 to produce a series of gas plugs flying through the trapping region. This allows, for example, ions to be cooled by these gas plugs as described above, but for the ions to be extracted during the gap time between plugs, thus further reducing any interaction between ions and gas during extraction process. Another valve could be located on the extraction path and open only during the time of ion extraction and transport towards the analyser, thus reducing or avoiding altogether the use of differential pumping. The pulsed valve could be piezoelectric or electromagnetic and operate either in pulsed manner or harmonically oscillating. The switching time of the valve or period of oscillations would preferably lies in the range of hundreds to thousands of microseconds.

If jet expansion is kept stable and is preferably accompanied by a reduced temperature of gas molecules and ions, the ions would experience a constant force along the direction of expansion. This force is proportional to their gas-dynamic cross-section and charge state, i.e. ion mobility. If a potential gradient is created by applying a voltage to aperture 20 to produce a counteracting electric force, ions of a particular ion mobility will equilibrate at a point on this potential slope where these two forces compensate each other, i.e. ion mobility separation in space could be performed. If the voltage on aperture 20 is varied or scanned, mobility-dependent extraction (scanning) of ions may be implemented. This could be used as a basis for an additional dimension of ion separation, with or without using a mass spectrometer for detection. For example, this separation could be used to separate singly-charged ions from multiply-charged ions.

The invention claimed is:

1. A method of changing the kinetic energy of ions, comprising:
    introducing ions from an ion source into a trapping region of an ion trap via a first aperture;
    trapping the ions in the trapping region of the ion trap, the ion trap being elongate along a first axis; and
    directing a beam of gas into and through the trapping region via a second aperture, so as to change the kinetic energy of the trapped ions thereby without substantial dissociation of the trapped ions;
    wherein the beam of gas propagates essentially along a single direction through the ion trapping region and all particles of the beam of gas have a vector of motion with a dominant component, the dominant component being common across all the particles; and
    wherein the first axis is arranged substantially collinearly to the direction of the beam of gas through the trapping region.

2. The method of claim 1, comprising:
    ejecting trapped ions from the ion trap along a second axis, the second axis being different from the first axis.

3. The method of claim 2, wherein the second axis is orthogonal to the first axis.

4. The method of claim 3, comprising injecting ions into the trap substantially along the first axis.

5. The method of claim 1, wherein the step of directing a gas comprises forming a gas jet.

6. The method of claim 1, further comprising:
receiving the gas at a gas inlet; and
wherein the pressure within the ion trap is less than the pressure on the other side of the gas inlet from the ion trap.

7. The method of claim 6, wherein the ion trap comprises a differential pumping aperture arranged along the first axis, the method further comprising:
creating a region of first pressure on the side of the differential pumping aperture that is closer to the gas inlet; and
creating a region of second pressure on the other side of the differential pumping aperture, the second pressure being lower than the first pressure.

8. The method of claim 7, wherein the differential pumping aperture is formed using a skimmer cone.

9. The method of claim 7, wherein the skimmer cone is located between the gas inlet and the location identified for the Mach disk of the gas flowing through the gas inlet.

10. The method of claim 1, wherein the pressure in the ion trap away from the beam is about $1 \times 10^{-4}$ mbar or less.

11. The method of claim 1, wherein a potential gradient is applied through the trapping region so as to cause separation of the ions based on their mobility.

12. The method of claim 1, further comprising:
applying a potential to the first aperture so as to cause separation of the ions based on their mobility.

13. The method of claim 1, wherein the step of trapping received ions uses a set of quadrupole rods.

14. The method of claim 2, wherein the trapping region comprises a circuit path, the circuit path including the first axis.

15. The method of claim 1, further comprising modulating the density of the gas beam.

16. An ion trap for changing the kinetic energy of ions, comprising:
an electrode arrangement elongated along a first axis and defining a trapping region that is in communication with a first aperture and with a second aperture;
a pumping arrangement; and
a controller, arranged to control the electrode arrangement to trap ions that are received, via the first aperture, within the trapping region, and to control the pumping arrangement to cause a beam of gas to be directed into and through the trapping region via the second aperture, so as to change the kinetic energy of the trapped ions thereby without substantial dissociation of the trapped ions;
wherein the beam of gas propagates essentially along a single direction through the ion trapping region and all particles of the beam of gas have a vector of motion with a dominant component, the dominant component being common across all the particles; and
wherein the first axis is arranged substantially collinearly to the direction of the beam of gas through the trapping region.

17. The ion trap of claim 16, wherein the controller is further configured to control the electrode arrangement to eject trapped ions from the ion trap along a second axis, the second axis being different from the first axis.

18. The ion trap of claim 17, wherein the second axis is orthogonal to the first axis.

19. The ion trap of claim 16, wherein the controller is further arranged to control the pumping arrangement so as to form a gas jet.

20. The ion trap of claim 16, wherein the controller is further arranged to control the pumping arrangement such that the pressure within the ion trap is less than the pressure outside of the gas inlet.

21. The ion trap of claim 20, further comprising:
a differential pumping aperture arranged along the first axis; and
wherein the controller is further arranged to control the pumping arrangement to create a region of first pressure on the side of the differential pumping aperture that is closer to the gas inlet, and
to create a region of second pressure on the other side of the differential pumping aperture, the second pressure being lower than the first pressure.

22. The ion trap of claim 21, wherein the differential pumping aperture is formed using a skimmer cone.

23. The ion trap of claim 22, wherein the skimmer cone is located between the gas inlet and the location identified for the Mach disk of the gas flowing through the gas inlet.

24. The ion trap of claim 16, wherein the controller is further arranged to control the pumping arrangement such that the pressure within the ion trap away from the beam is about $1 \times 10^{-4}$ mbar or less.

25. The ion trap of claim 23, wherein the first aperture is arranged to receive a potential so as to cause ion mobility separation of the ions.

26. The ion trap of claim 16, wherein the electrode arrangement comprises a set of quadrupole rods.

27. The ion trap of claim 16, wherein the electrode arrangement is configured in a circuit path including the first axis, and wherein the controller is further arranged to control the electrode arrangement such that the trapping region comprises the circuit path.

28. A mass spectrometer, comprising:
an electrode arrangement elongated along a first axis and defining a trapping region that is in communication with a first aperture and with a second aperture;
a pumping arrangement;
a controller, arranged to control the electrode arrangement to trap ions that are received, via the first aperture, within the trapping region, and to control the pumping arrangement to cause a beam of gas to be directed into and through the trapping region via the second aperture, so as to change the kinetic energy of the trapped ions thereby without substantial dissociation of the trapped ions; and
a mass analyser, arranged to receive cooled ions from the ion trap;
wherein the beam of gas propagates essentially along a single direction through the ion trapping region and all particles of the beam of gas have a vector of motion with a dominant component, the dominant component being common across all the particles; and
wherein the first axis is arranged substantially collinearly to the direction of the beam of gas through the trapping region.

29. A mass spectrometer according to claim 28, wherein the mass analyser comprises one of: an orbitrap-type mass analyser; a time-of-flight mass analyser; or a time-of-flight mass analyser comprising at least one of multi-turn or multi-reflecting configurations.

* * * * *